US009398844B2

(12) United States Patent
Ambrus et al.

(10) Patent No.: US 9,398,844 B2
(45) Date of Patent: Jul. 26, 2016

(54) COLOR VISION DEFICIT CORRECTION

(75) Inventors: Tony Ambrus, Seattle, WA (US); Adam Smith-Kipnis, Seattle, WA (US); Stephen Latta, Seattle, WA (US); Daniel McCulloch, Kirkland, WA (US); Brian Mount, Seattle, WA (US); Kevin Geisner, Mercer Island, WA (US); Ian McIntyre, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 435 days.

(21) Appl. No.: 13/526,315

(22) Filed: Jun. 18, 2012

(65) Prior Publication Data

US 2013/0335435 A1    Dec. 19, 2013

(51) Int. Cl.
| | |
|---|---|
| *G06T 19/00* | (2011.01) |
| *A61B 3/06* | (2006.01) |
| *G06T 19/20* | (2011.01) |
| *G09G 3/00* | (2006.01) |
| *G09G 5/02* | (2006.01) |
| *G02B 27/01* | (2006.01) |

(52) U.S. Cl.
CPC .............. *A61B 3/066* (2013.01); *G06T 19/006* (2013.01); *G06T 19/20* (2013.01); *G02B 2027/0178* (2013.01); *G06T 2210/41* (2013.01); *G06T 2219/2012* (2013.01); *G09G 3/003* (2013.01); *G09G 5/026* (2013.01); *G09G 2380/08* (2013.01)

(58) Field of Classification Search
CPC ..................... G02B 2027/0178; G02B 27/017; G02B 2027/0132; G02B 2027/0118; G02B 2027/0134; G06T 19/006
See application file for complete search history.

(56) References Cited

U.S. PATENT DOCUMENTS

| | | | |
|---|---|---|---|
| 5,467,123 A | 11/1995 | Zeevi et al. | |
| 6,169,526 B1 * | 1/2001 | Simpson et al. | .................. 345/8 |
| 6,727,807 B2 * | 4/2004 | Trajkovic et al. | ............. 340/436 |
| 7,124,375 B1 | 10/2006 | Steele et al. | |
| 7,394,468 B2 | 7/2008 | Hofman et al. | |

(Continued)

FOREIGN PATENT DOCUMENTS

| | | |
|---|---|---|
| CA | 2750287 A1 | 11/2011 |
| JP | 2006153909 A | 6/2006 |

(Continued)

OTHER PUBLICATIONS

Peli et al., "Development and Evaluation of Vision Multiplexing Devices for Vision Impairments," Int J Artif Intell Tools. Authors manuscript; PMC, Jun. 1, 2010.*

(Continued)

*Primary Examiner* — Kee M Tung
*Assistant Examiner* — Nicholas R Wilson
(74) *Attorney, Agent, or Firm* — Dan Choi; Judy Yee; Micky Minhas

(57) ABSTRACT

Embodiments related to improving a color-resolving ability of a user of a see-thru display device are disclosed. For example, one disclosed embodiment includes, on a see-thru display device, constructing and displaying virtual imagery to superpose onto real imagery sighted by the user through the see-thru display device. The virtual imagery is configured to accentuate a locus of the real imagery of a color poorly distinguishable by the user. Such virtual imagery is then displayed by superposing it onto the real imagery, in registry with the real imagery, in a field of view of the user.

20 Claims, 10 Drawing Sheets

(56) References Cited

U.S. PATENT DOCUMENTS

| | | | |
|---|---|---|---|
| 7,945,092 B2 | 5/2011 | Hayashi et al. | |
| 2003/0197693 A1* | 10/2003 | Karstens | 345/204 |
| 2004/0136570 A1 | 7/2004 | Ullman et al. | |
| 2005/0156942 A1 | 7/2005 | Jones | |
| 2007/0182755 A1 | 8/2007 | Jones et al. | |
| 2007/0236656 A1 | 10/2007 | Jeong et al. | |
| 2008/0079750 A1 | 4/2008 | Setlur | |
| 2008/0157946 A1* | 7/2008 | Eberl et al. | 340/435 |
| 2008/0278821 A1 | 11/2008 | Rieger | |
| 2009/0327883 A1* | 12/2009 | Robertson et al. | 715/273 |
| 2010/0158310 A1* | 6/2010 | McQueen | G06K 9/00 382/100 |
| 2010/0182337 A1 | 7/2010 | Asakura | |
| 2011/0043644 A1* | 2/2011 | Munger et al. | 348/207.1 |
| 2011/0229023 A1 | 9/2011 | Jones et al. | |
| 2012/0147163 A1 | 6/2012 | Kaminsky | |

FOREIGN PATENT DOCUMENTS

| | | | |
|---|---|---|---|
| KR | 20130030667 A | 3/2013 |
| WO | 9639919 A1 | 12/1996 |

OTHER PUBLICATIONS

Greenberg, Andy, "Security Guru Launches iPhone App to Hack Colorblindness", retreived at [[http://www.forbes.com/sites/andygreenberg/2010/12/15/security-guru-launches-iphone-app-to-hack-colorblindness/#more-2018]]; Dec. 15, 2010, 5 pages.

European Patent Office, Search Report Received for European Patent Application No. 13197840.5, May 22, 2014, 10 Pages.

ISA European Patent Office, International Search Report and Written Opinion of PCT/US2013/046145, Sep. 12, 2013, Netherlands, 8 pages.

"Daltonism Correction," Nicolas Guillaume, https://play.google.com/store/apps/details?id=fr.nghs.android.cbs.enhancer&hl=en, Android Apps on Google Play, Updated Sep. 25, 2011, Accessed Apr. 11, 2012, 2 pages.

The State Intellectual Property Office of China, First Office Action and Search Report Issued in Chinese Patent Application No. 201310757256.2, Feb. 2, 2016, China, 14 pages.

* cited by examiner

COLOR VISION DEFICIT CORRECTION

BACKGROUND

Many people have difficulty distinguishing one color from another. This condition is called 'color vision deficiency', and is known colloquially as 'color blindness'. Several different forms of color vision deficiency are recognized, including red-green dichromacy (protanopia, deuteranopia), anomalous red-green trichromacy (protanomaly and deuteranomaly), blue-yellow dichromacy (tritanopia) and anomalous blue-yellow trichromacy (tritanomaly). Each form is caused by the expression of a recessive genetic trait that reduces the variety of retinal cones in the affected person's eyes, or makes some of the cones less sensitive. Carried primarily on the Y chromosome, these traits may affect 7 to 10% of the male population, and about 0.5% of the female population. Total color blindness (monochromacy) is also recognized, as are injury-related color vision defects.

In society, color vision deficiency may cause some degree of disability. For example, it may tax an affected person's ability to decipher traffic signals or other signage. It may disqualify the person for employment in fields where acute color vision is required. Moreover, a color vision deficit may occlude the affected person's overall perception—and enjoyment—of the visual world. Unfortunately, there is no medical cure or treatment for color vision deficiency.

SUMMARY

One embodiment of this disclosure provides a method to improve a color-resolving ability of a user of a see-thru display device. Enacted within the see-thru display device, this method includes constructing and displaying virtual imagery to superpose onto real imagery sighted by the user through the see-thru display device. The virtual imagery is configured to accentuate a locus of the real imagery of a color poorly distinguishable by the user. Such virtual imagery is then displayed by superposing it onto the real imagery, in registry with the real imagery, in a field of view of the user.

This Summary is provided to introduce in simplified form a selection of concepts that are further described in the Detailed Description. This Summary is not intended to identify key features or essential features of the claimed subject matter, nor is it intended to be used to limit the scope of the claimed subject matter. Furthermore, the claimed subject matter is not limited to implementations that solve any disadvantages noted in any part of this disclosure.

DETAILED DESCRIPTION

Figure 1B:
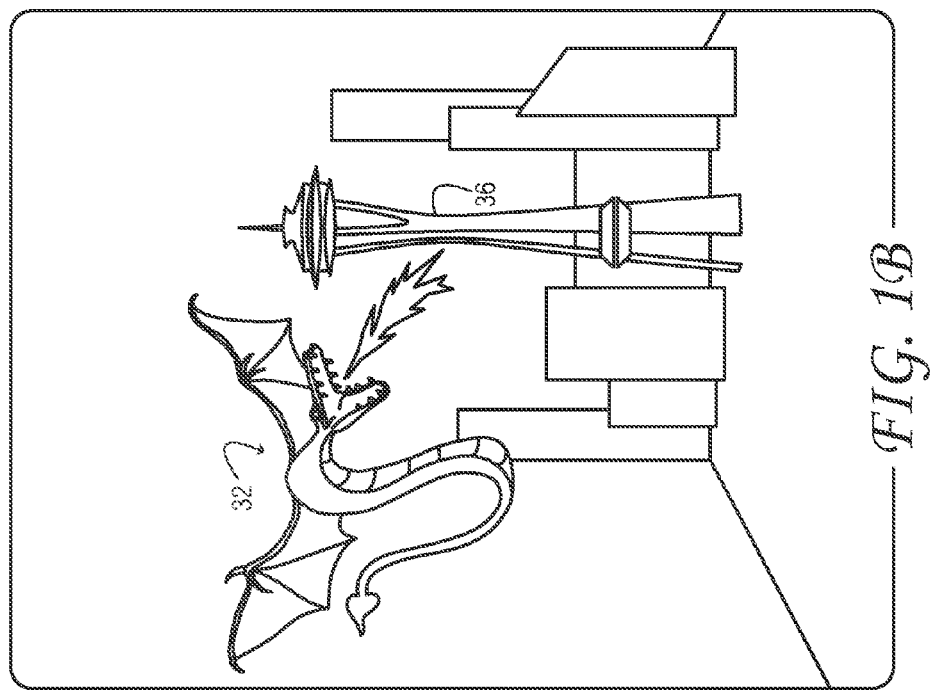
FIG. 1B shows an example view of a user in the augmented-reality environment of FIG. 1A.

Aspects of this disclosure will now be described by example and with reference to the illustrated embodiments listed above. Components, process steps, and other elements that may be substantially the same in one or more embodiments are identified coordinately and are described with minimal repetition. It will be noted, however, that elements identified coordinately may also differ to some degree. It will be further noted that the drawing figures included in this disclosure are schematic and generally not drawn to scale. Rather, the various drawing scales, aspect ratios, and numbers of components shown in the figures may be purposely distorted to make certain features or relationships easier to see.

This disclosure describes embodiments of augmented-reality (AR) approaches for improving a person's color-resolving ability. AR enables a person to view real-world imagery together with computer-generated, virtual imagery. An AR system may include a see-thru display device, which the person wears, and through which real and virtual imagery are combined in the same field of view. Such a device may be incorporated into goggles, a helmet, glasses, or other eyewear.

Figure 1A:
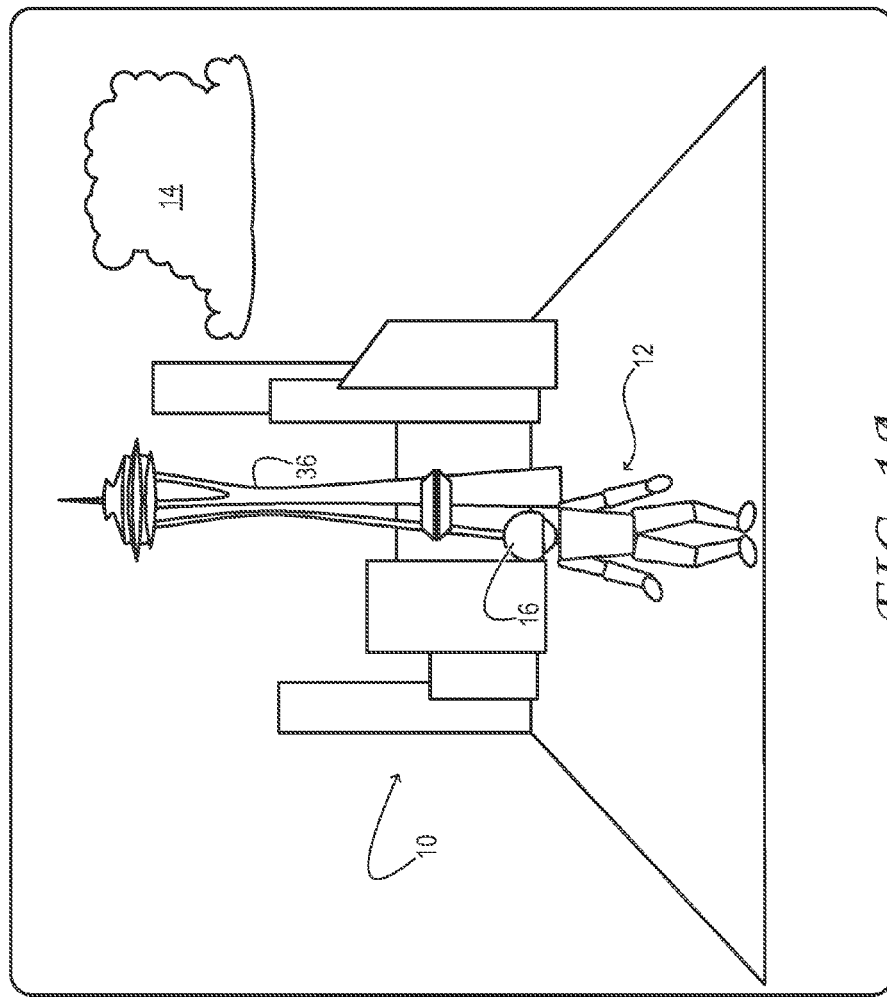
FIG. 1A shows aspects of an augmented-reality environment in accordance with an embodiment of this disclosure.

Prior to discussing these embodiments in detail, aspects of an example AR environment 10 is described with reference to FIG. 1A. To experience an augmented reality, a user 12 may employ an AR system having suitable display, sensory, and computing hardware. In the embodiment shown in FIG. 1A, the AR system includes cloud 14 and see-thru display device 16. 'Cloud' is a term used to describe a computer system accessible via a network and configured to provide a computing service. In the present context, the cloud may include any number of computers.

See-thru display device 16 is a wearable device configured to present real and virtual imagery to its wearer—i.e., user 12. More specifically, the see-thru display device enables the user to view real-world imagery in combination with computer-generated, virtual imagery. Imagery from both sources is presented in the user's field of view, and may appear to share the same physical space. This scenario is represented in FIG. 1B, which shows an example view of user 12 that includes virtual imagery (a dragon) viewable along with real-world objects. As described below in further detail, the see-thru display device may include a computer. Accordingly, some of the computer programs furnishing the AR environment may be executed within the see-thru display device. Others may be executed within cloud 14, which is operatively coupled to the see-thru display device via one or more wireless communication links. Such links may include cellular, Wi-Fi, and others.

In some scenarios, the computer programs furnishing the AR experience may include a game. More generally, the programs may be any that combine computer-generated, virtual imagery with the real-world imagery. A realistic AR experience may be achieved with each user viewing his environment naturally, through transparent optics of the see-thru display device. The virtual imagery, meanwhile, is projected into the same field of view in which the real imagery is received.

Figure 2:
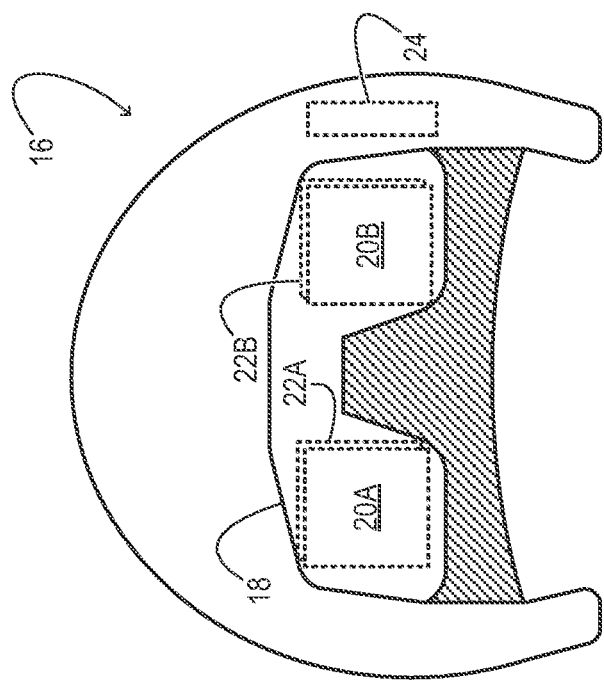

FIG. 2 shows an example see-thru display device 16 in one embodiment. See-thru display device 16 is a helmet having a controllable dimming filter 18 in the form of a visor. The dimming filter may be configured for glare reduction and/or brightness reduction of the real imagery received through the see-thru display device. Between the dimming filter and each of the wearer's eyes is arranged a microdisplay 20 and an eye tracker 22: microdisplay 20A and eye tracker 22A are arranged in front of the right eye; microdisplay 20B and eye tracker 22B are arranged in front of the left eye. Although the eye trackers are arranged behind the microdisplays in the drawing, they may instead be arranged in front of the microdisplays, or distributed in various locations within the see-thru display device. See-thru display device 16 also includes computer 24. The computer is operatively coupled to both microdisplays and to both eye trackers.

Each microdisplay 20 may be at least partly transparent, providing a substantially unobstructed field of view in which the user can directly observe his physical surroundings. Each microdisplay is configured to present, in the same field of view, virtual imagery in the form of a computer-generated display image. The virtual imagery is superposed onto the real imagery sighted by the user of the see-thru display device, in registry with the real imagery. In other words, the real and virtual imagery share a common coordinate system, so that a virtual dragon—for example—hovering 50 meters north of a real building stays in the correct position relative to the building even if the user turns his head.

Continuing in FIG. 2, computer 24 controls the internal componentry of microdisplays 20A and 20B in order to form the desired display images. In one embodiment, computer 24 may cause microdisplays 20A and 20B to display the same image concurrently, so that the wearer's right and left eyes receive the same image at the same time. In another embodiment, the microdisplays may project stereoscopically related images concurrently, so that the wearer perceives a three-dimensional image. In one scenario, the computer-generated display image and various real images of objects sighted through the microdisplay may occupy different focal planes. Accordingly, the wearer observing a real-world object may have to shift his corneal focus in order to resolve the display image. In other scenarios, the display image and at least one real image may share a common focal plane.

Each eye tracker 22 comprises a detector configured to detect an ocular state of the wearer of see-thru display device 16. The eye tracker may determine a position of a pupil of the wearer's eye, locate a line of sight of the wearer and/or measure an extent of iris closure. If two substantially equivalent eye trackers are included, one for each eye, they may be used together to determine the focal plane of the wearer based on the point of convergence of the lines of sight of the wearer's left and right eyes. This information may be used for placement of one or more virtual images, for example.

Figure 3:
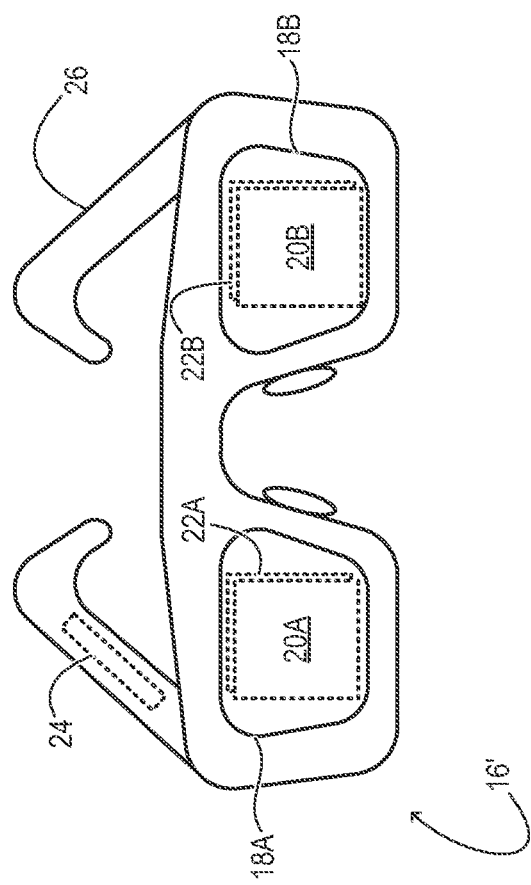
FIGS. 2 and 3 show example see-thru display devices in accordance with embodiments of this disclosure.

FIG. 3 shows another example see-thru display device 16'. See-thru display device 16' is an example of AR eyewear. It may closely resemble an ordinary pair of eyeglasses or sunglasses, but it too includes microdisplays 20A and 20B, and eye trackers 22A and 22B, which are arranged behind dimming filters 18A and 18B. See-thru display device 16' includes wearable mount 26, which positions the microdisplays and eye trackers a short distance in front of the wearer's eyes. In the embodiment of FIG. 3, the wearable mount takes the form of conventional eyeglass frames.

No aspect of FIG. 2 or 3 is intended to be limiting in any sense, for numerous variants are contemplated as well. In some embodiments, for example, a binocular microdisplay extending over both eyes may be used instead of the monocular microdisplays shown in the drawings. Likewise, a see-thru display device may include a binocular eye tracker. In some embodiments, an eye tracker and microdisplay may be integrated together, and may share one or more components.

Figure 4:
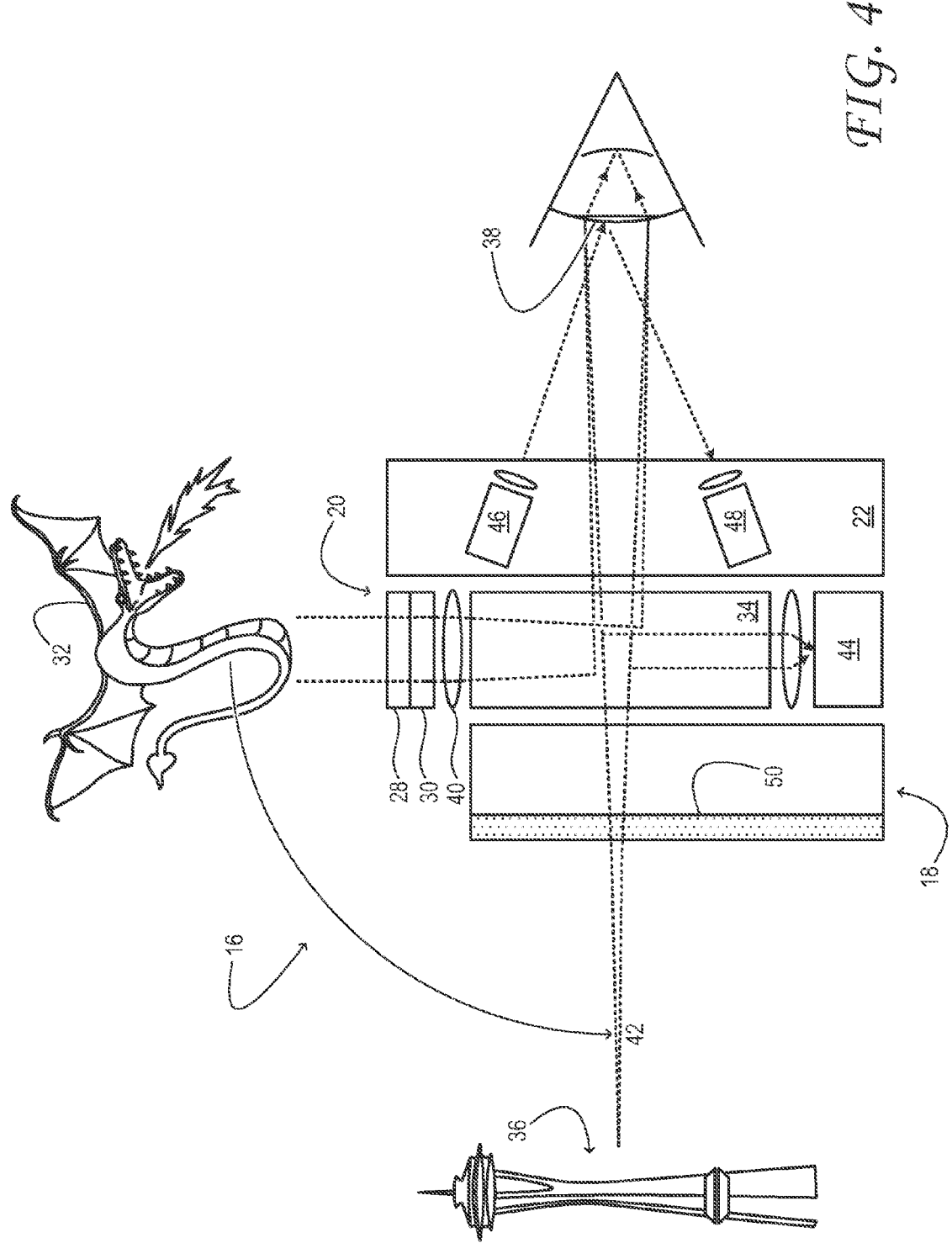
FIG. 4 shows aspects of example optical componentry of a see-thru display device in accordance with an embodiment of this disclosure.

FIG. 4 shows aspects of example optical componentry of see-thru display device 16. In the illustrated embodiment, microdisplay 20 includes illuminator 28 and image former 30. The illuminator may comprise a white light source, such as a white light-emitting diode (LED). The illuminator may further comprise an optic suitable for collimating the emission of the white light source and directing the emission into the image former. The image former may comprise a rectangular array of light valves, such as a liquid-crystal display (LCD) array. The light valves of the array may be arranged to spatially vary and temporally modulate the collimated light transmitted therethrough, so as to form pixels of a display image 32. Further, the image former may comprise suitable light-filtering elements in registry with the light valves so that the display image formed is a color image. The information content of display image 32 may be supplied to microdisplay 20 as any suitable data structure—a digital image or digital video data structure, for example.

In another embodiment, illuminator 28 may comprise one or more modulated lasers, and image former 30 may be a moving optic configured to raster the emission of the lasers in synchronicity with the modulation to form display image 32. In yet another embodiment, image former 30 may comprise a rectangular array of modulated color LEDs arranged to form the display image. As each color LED array emits its own light, illuminator 28 may be omitted from this embodiment. The various active components of microdisplay 20, including image former 30, are operatively coupled to computer 24. In particular, the computer provides suitable control signals that, when received by the image former, cause the desired display image to be formed.

Continuing in FIG. 4, microdisplay 20 includes multipath optic 34. The multipath optic is suitably transparent, allowing external imagery—e.g., a real image 36 of a real object—to be sighted directly through it. Image former 30 is arranged to project display image 32 into the multipath optic. The multipath optic is configured to reflect the display image to pupil 38 of the wearer of see-thru display device 16. To reflect the display image as well as transmit the real image to pupil 38, multipath optic 34 may comprise a partly reflective, partly transmissive structure.

In some embodiments, multipath optic 34 may be configured with optical power. It may be used to guide display image 32 to pupil 38 at a controlled vergence, such that the display image is provided as a virtual image in the desired focal plane. In other embodiments, the position of the virtual display image may be determined by the converging power of lens 40. In one embodiment, the focal length of lens 40 may be adjustable, so that the focal plane of the display image can be moved back and forth in the wearer's field of view. In FIG. 4, an apparent position of virtual display image 32 is shown, by example, at 42. In other embodiments, the focal length of lens 40 may be fixed, such that the focal plane of the display image is maintained at or near infinity. Nevertheless, the apparent focal plane of the display image can still be moved back and forth by providing stereoscopically related images to the microdisplays of each eye.

FIG. 4 also shows camera 44, which receives the real imagery sighted through see-thru display device 16 by the wearer of the see-thru display device. In the embodiment illustrated in FIG. 4, the camera receives the real imagery via multipath optic 34, which splits the real imagery into a first portion that passes through to pupil 38, and a second portion focused on the camera. In this configuration, camera 44 may be referred to as a 'front-facing' camera, regardless of the actual orientation of its aperture.

FIG. 4 also shows aspects of eye tracker 22, which includes illuminator 46 and detector 48. The illuminator may include a low-power infrared LED or diode laser. In one embodiment, the illuminator may provide periodic illumination in the form of narrow pulses—e.g., 1 microsecond pulses spaced 50 microseconds apart. The detector may be any camera suitable for imaging the wearer's eye in enough detail to resolve the pupil. More particularly, the resolution of the detector may be sufficient to enable estimation of the position of the pupil with respect to the eye orbit, as well as the extent of closure of the iris. In one embodiment, the aperture of the detector is equipped with a wavelength filter matched in transmittance to the output wavelength band of the illuminator. Further, the detector may include an electronic 'shutter' synchronized to the pulsed output of the illuminator.

FIG. 4 also shows aspects of controllable dimming filter 18, on which cross-polarizing layer 50 is arranged. The cross-polarizing layer is configured to decrease the transmittance of the see-thru display device to the real imagery viewed by the wearer. In one embodiment, the cross-polarizing layer may include an electrically polarizable liquid crystal; the transmittance may be decreased by increasing a polarization applied to the liquid crystal.

In addition to providing a premium AR experience, the configurations described above may be used for certain other purposes. For example, a suitably configured see-thru display device may be used to remedy a color vision deficit or to provide its wearer with extended color vision. More particularly, the configurations described herein enable various methods to improve a color-resolving ability of a user of a see-thru display device. Some such methods are now described, by way of example, with continued reference to the above configurations. It will be understood, however, that the methods here described, and others fully within the scope of this disclosure, may be enabled by other configurations as well. Further, some of the process steps described and/or illustrated herein may, in some embodiments, be omitted without departing from the scope of this disclosure. Likewise, the indicated sequence of the process steps may not always be required to achieve the intended results, but is provided for ease of illustration and description. One or more of the illustrated actions, functions, or operations may be performed repeatedly, depending on the particular strategy being used.

Figure 5:
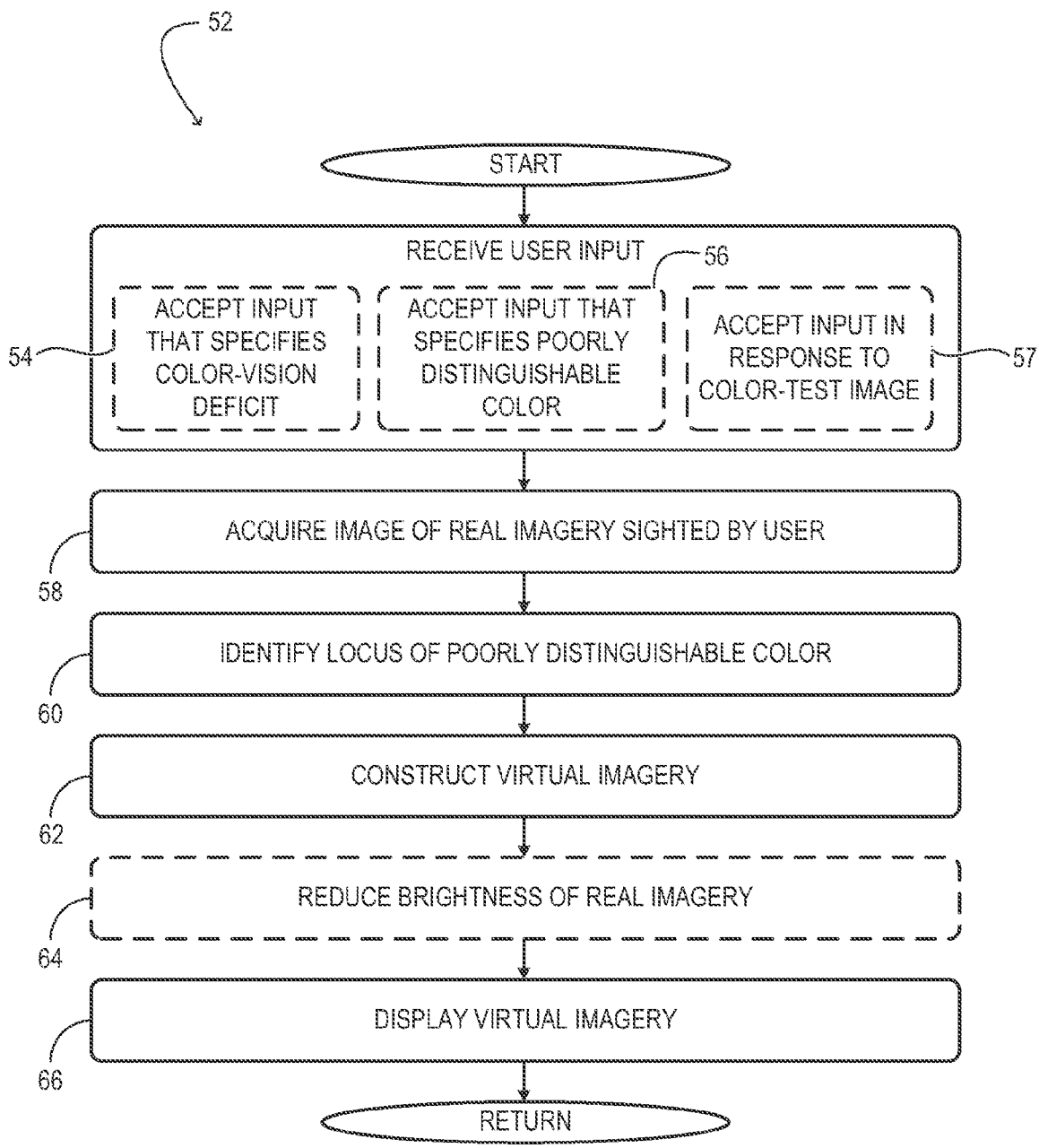
FIG. 5 illustrates an example method to improve the color-resolving ability of a user of a see-thru display device in accordance with an embodiment of this disclosure.

FIG. 5 illustrates an example method 52 to improve the color-resolving ability of a user of a see-thru display device, such as see-thru display device 16. This method may be enacted from within the see-thru display device, at least partially in the cloud, or in any other suitable manner.

At the outset of method 52, input from the user may be accepted by the see-thru display device to help determine how to augment the appearance of colors for the user. The input may control, directly or indirectly, which color or colors are to be accentuated by the see-thru display device. Various modes of operation are envisaged herein. For example in one embodiment, at 54, the user may specify the particular type of color vision deficit that he or she experiences—e.g., protanopia, deuteranopia, protanomaly, deuteranomaly, tritanopia, or tritanomaly. Optionally, the input may also specify a degree or severity of the color vision deficit. In another embodiment, at 56 the user may specify one or more colors in the real imagery that should be accentuated—e.g., red, green, blue, yellow, or no color at all. In a typical scenario, the specified color would be a color poorly distinguishable by the user's unaided eye.

In yet another embodiment, at 57, user input may be received in response to visual tests presented to the user to allow the see-thru display device to determine a condition to be corrected. As a more specific example, the see-thru display device may display one or more images, such as Ishihara color test images, used to test for color vision deficiencies, and one or more user inputs in the form of responses to those images may be received. Based upon the results of such color tests, the see-thru display device may be calibrated to adapt to the color vision deficiency or deficiencies of the particular user.

In still other embodiments, the see-thru display device could be configured to discern color-vision deficiency indirectly, and unbeknownst to the user. For instance, the device may be configured to measure how long it takes the user to select a green icon on a red metro tile versus a blue icon on a red metro tile. Extended time to select the green icon may indicate some form of red-green color deficit. Additionally or alternatively, the device may be configured to measure the length of time that the user spends looking at selected aspects of a scene—aspects that would be difficult to discern for a person with a color-vision deficit. This latency could be compared to an average latency among users viewing the same or similar scenes. Effectively, the device could assess whether a logo on a building jumps out to the user as quickly as it does to an average person. If not, a color-vision deficit may be indicated.

In the various embodiments contemplated herein, the user input accepted in method 52 may specify a color vision deficit, a color to accentuate, both a deficit and a color, or neither. Moreover, the user input may take any suitable form—from spoken input, gesture input received via an outward-facing image sensor as described above, from a preference file stored in removable memory or in cloud 14, and/or in any other suitable manner.

Continuing in FIG. 5, at 58 an image of the real imagery sighted by the user is acquired. In one embodiment, the image may be acquired using a front-facing camera of the see-thru display device, as noted above.

At 60 a locus of a color poorly distinguishable by the user is identified from the acquired image and submitted for further processing. The locus referred to herein may be one of a plurality of contiguous or non-contiguous loci identified and submitted for further processing. In embodiments in which a particular color was specified by user input, one or more loci of that color may be identified. For example, if the user input says "Show me everything red," then a locus comprising all red-colored pixels of the acquired image may be identified. In embodiments in which a particular color vision deficit was specified by user input, the locus may be identified based on the nature of the deficit. For example, if the user identifies himself as exhibiting deuteranomaly, then one of two possible scenarios may be enacted. Either a locus comprising all red-colored pixels or all green-colored pixels of the image may be identified and submitted for further processing. In one embodiment, the decision of whether to identify red pixels or green pixels may be based on a preference of the user. In another embodiment, it may be based on the relative prevalence of red and green in the real imagery. For instance, it may be desirable to identify the color that is less prevalent in the real imagery.

In these and other embodiments, identifying a locus of a color poorly distinguishable by the user may include recognizing an object in the acquired image. In a typical scenario, objects to be recognized may include signage of various kinds—road signs, warning signs, stop signs, etc. For example, any locus having the octagonal shape of a stop sign may be identified from the acquired image, irrespective of whether the see-thru display device can discern that the locus is colored red. Machine vision, in some cases, may have difficulty determining color reliably under low-light conditions, or in the presence of intense specular reflection.

At 62 of method 52, virtual imagery is constructed that will be superposed onto the real imagery sighted by the user through the see-thru display device. This virtual imagery may be configured to accentuate the locus of the real imagery identified above—i.e., the locus of the color poorly distinguishable by the user. More particularly, the virtual imagery may be constructed based on the image of the real imagery acquired at 58.

Figure 7:
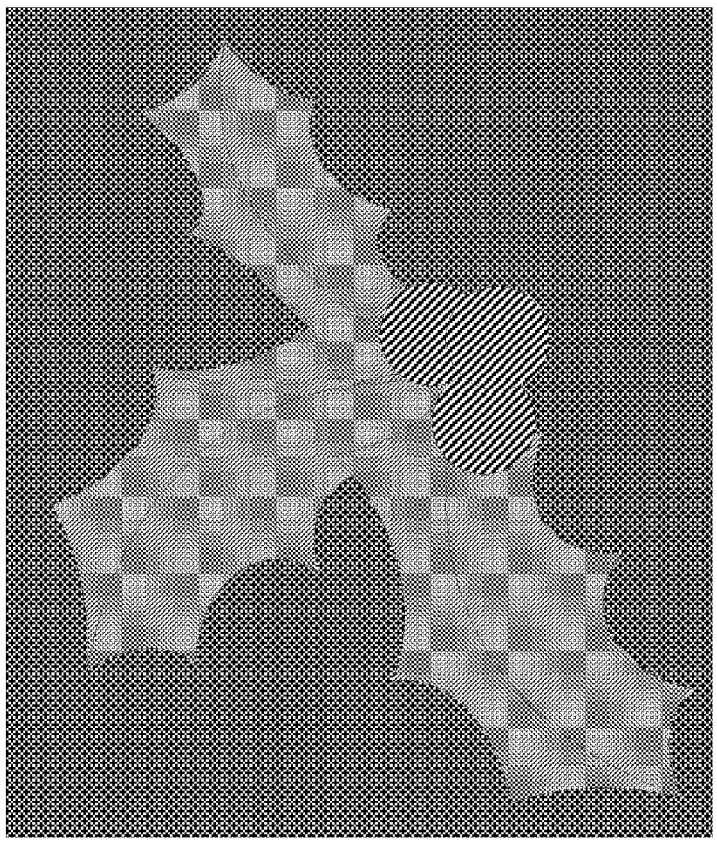
FIGS. 7 through 13 illustrate examples of how the real imagery of FIG. 6 may look to a deuteranomalous person on application of the methods described herein.
Figure 6:
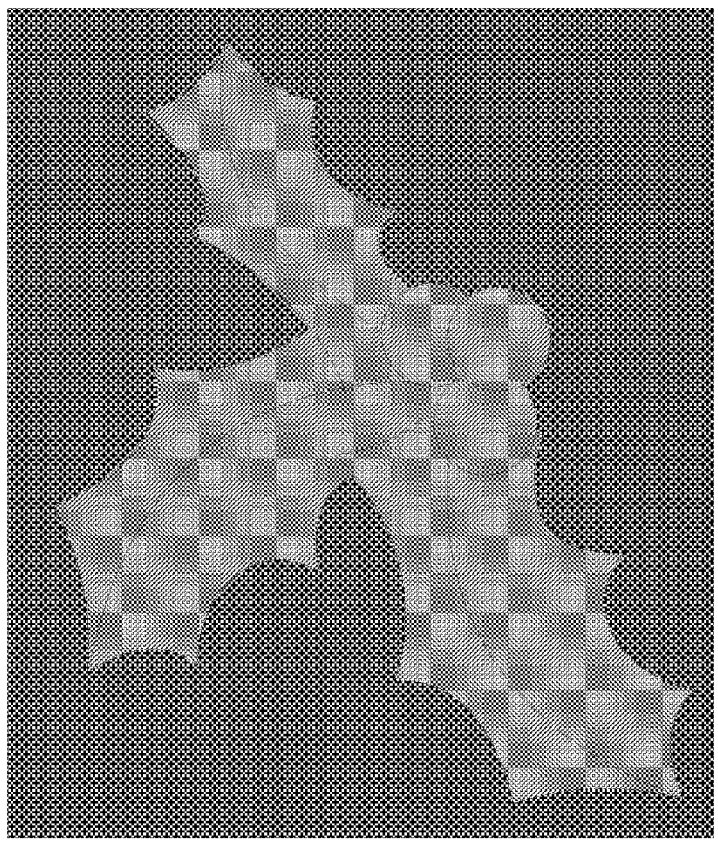
FIG. 6 represents how selected real imagery may look to a deuteranomalous person prior to application of the methods described herein.

In one embodiment, the virtual imagery may be configured to shift the color of the locus to a color more distinguishable by the user. This approach takes advantage of the additivity of real and virtual imagery in the see-thru display device. For instance, a green-colored locus can be made to appear bluer by overlaying a congruent violet-colored locus of suitable intensity. A user exhibiting any form of red-green color vision deficiency will find the augmented locus easier to distinguish than the original green-colored locus, especially from a red background. This approach is illustrated in FIGS. 6 and 7, with FIG. 6 representing how the holly sprig might look to a deuteranomalous person prior to accentuation of the red berries, and FIG. 7 representing how it might look after accentuation. In such embodiments, a controllable dimming filter arranged in the see-thru display device may be configured to controllably reduce the brightness of the real imagery in order to achieve the desired overall brightness level. In some scenarios, judicious use of the dimming filter for color shifting may enable the microdisplays to operate at lower power, thereby extending battery life.

Figure 8:
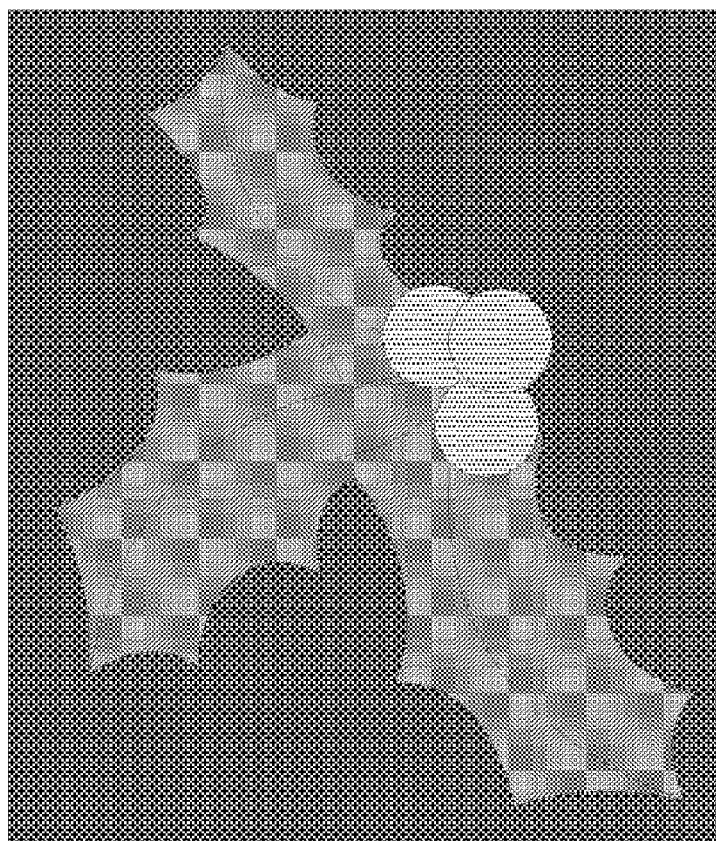

In another embodiment, the virtual imagery may be configured simply to increase the brightness of the identified locus without changing the color. This approach may be useful for users with a mild color vision impairment. It may involve brightening every red locus to make it more red, and/or brightening every green locus to make it more green. By increasing the brightness of these colors, the mildly impaired user may find the colors easier to distinguish. This approach is illustrated in FIG. 8.

In another embodiment, the virtual imagery may be configured to shift the color or increase the brightness of the identified locus differently for the right and left eyes. For example, the virtual imagery may brighten the green of the left eye and the red of the right eye, or vice versa. The user having a red-green color deficit may be able to learn to associate the differential brightening with different colors over time, just as people learn to accommodate the red and green bias of red/green 3D glasses after only a few minutes. In embodiments that include a subtractive display, the red and green colors in the identified locus may be dimmed instead of brightened.

Figure 9:
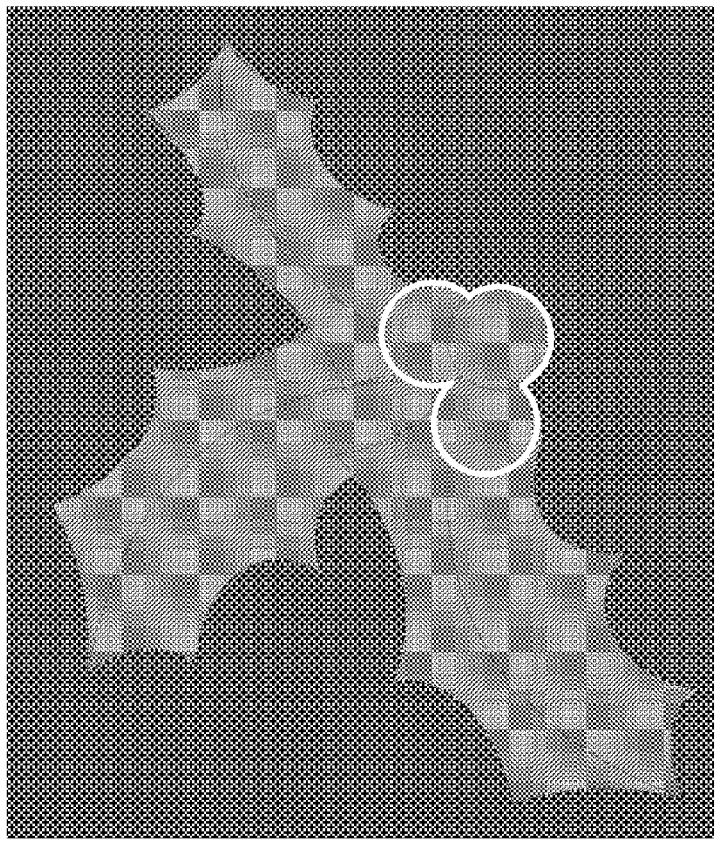

In another embodiment, the virtual imagery may be configured to delineate a perimeter of the locus. If the locus of the real imagery is a red locus, for example, the virtual imagery may include a narrow line rendered in cyan (the color complement of red). If the intensity of the virtual imagery is chosen to balance that of the real imagery, then the red locus will appear outlined in white, as shown in FIG. 9. It will be understood, however, that a perimeter of any color brighter than the original locus is achievable according to this approach. Again, a controllable dimming filter may be used to reduce the brightness of the real imagery in some situations.

Figure 11:
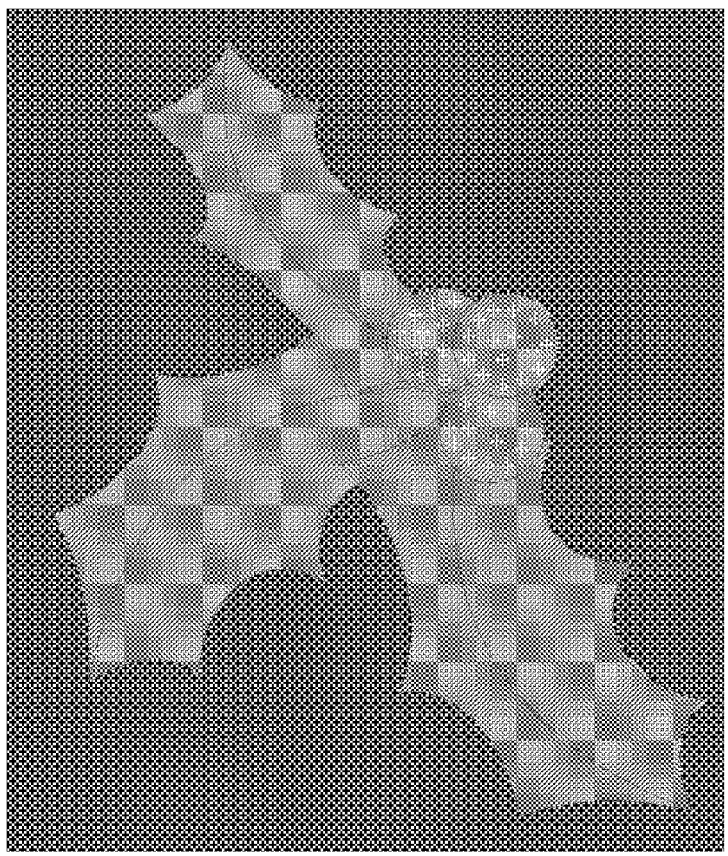
Figure 10:
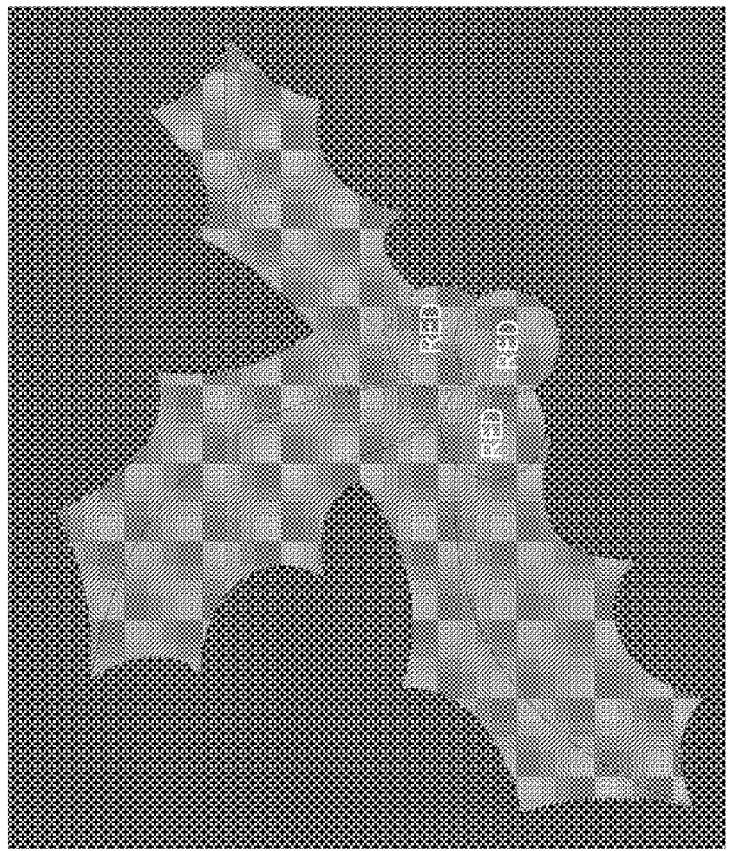
Figure 12:

In another embodiment, the virtual imagery may be configured to overwrite the locus with text—e.g., white text using the color complement of the locus in the virtual imagery, or, text of any color brighter than and/or having suitable contrast with the original locus in light of the particular color vision deficiency of the user. This approach is illustrated in FIG. 10. In another embodiment, the virtual imagery may be configured to overwrite the locus with a symbol or a segmentation pattern, as shown in FIGS. 11 and 12, respectively.

Figure 13:
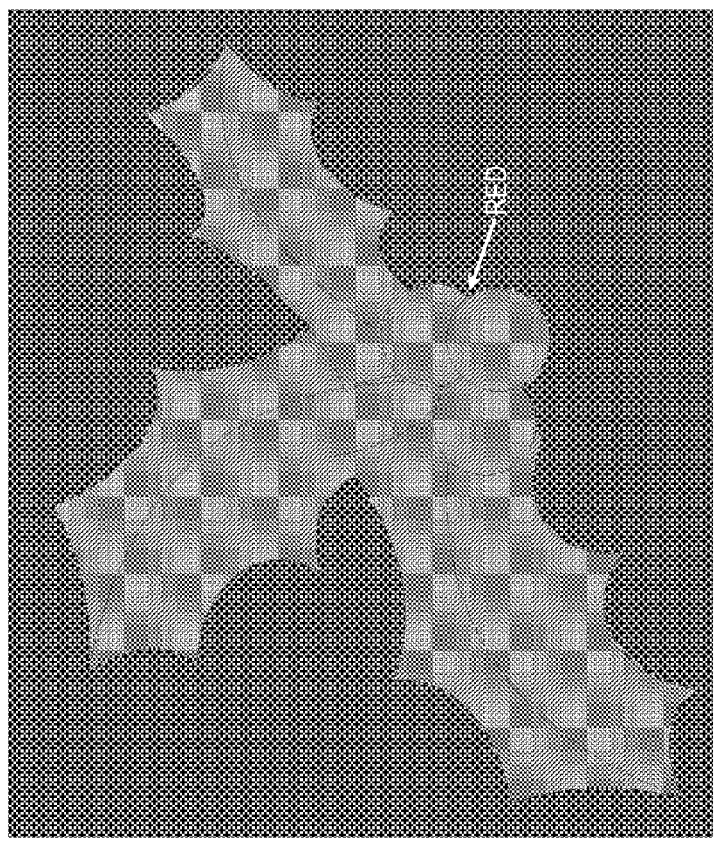

In still other embodiments, the virtual imagery may be configured to write text and/or a symbol adjacent to the locus. This approach is shown in FIG. 13. It will be understood that the virtual imagery may be configured to enact various combinations of the locus-accentuation approaches identified above. For example, a given locus can be presented color-shifted and segmented, if desired.

As noted above, in embodiments in which a locus is identified via object recognition, the virtual imagery may be constructed further based on the nature of the recognized object. In particular, the virtual imagery may be constructed to accentuate the recognized object over and beyond other loci accentuated by the virtual imagery. Autumn leaves can be red, for example, and so can a stop sign. In a scenario in which all red pixels are accentuated, the stop sign may be differently accentuated, or more highly accentuated, or in general, can be accentuated in a manner that is not compromised by the accentuation of the leaves. In this manner, the user's ability to distinguish a recognized object related to safety is given a higher priority.

Returning now to FIG. 5, at 64 the brightness of the real imagery sighted by the wearer is optionally reduced via a dimming filter of the see-thru display device. The amount of brightness reduction may be as needed to effect the desired level of overall brightness in the augmented imagery perceived by the user, to provide color shifting at reduced power, etc. At 66 the virtual imagery constructed as described above is displayed. More particularly, the virtual imagery is superposed onto the real imagery sighted by the user of the see-thru display device, in registry with the real imagery, in the user's field of view.

No aspect of FIG. 5 should be understood in a limiting sense, for numerous variants and extensions are contemplated as well. For instance, a user of a see-thru display device may, in some scenarios, desire assistance in identifying matching colors—in a wardrobe, for example. Here, the virtual imagery may be constructed in such a way that a plurality of loci of matching colors in a real image are accentuated by overwriting the loci of such colors with one or more of text, a symbol, and a segmentation pattern, to indicate the matching colors.

In other embodiments, the methodology presented herein may be fine tuned with the aid of an eye tracker arranged in the see-thru display device. In one example, the eye tracker may be configured to track the focal point of the user. The virtual imagery constructed at 62 of the above method may be configured to accentuate the locus of poor distinguishability to a greater degree when that locus is near to the focal point than when the locus is far from the focal point. The approach may be useful for reducing the virtual 'clutter' in the user's field of view, or for targeting computational effort in the area that is actually being sighted.

Figure 14:
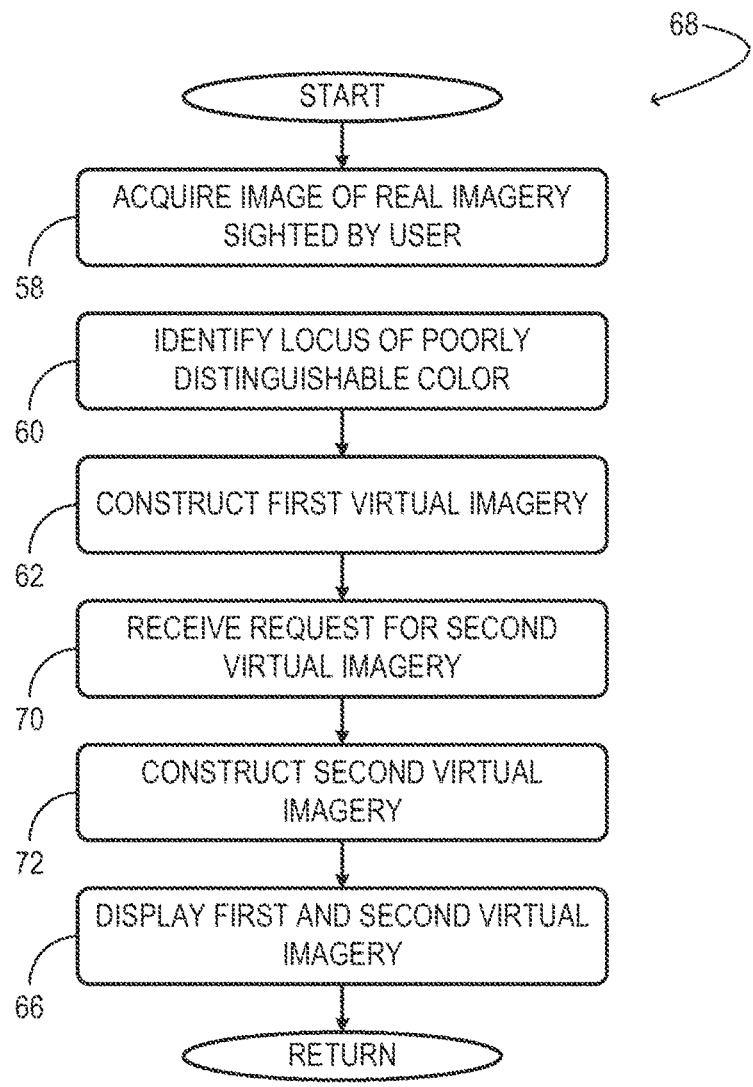
FIG. 14 illustrates another example method to improve the color-resolving ability of a user of a see-thru display device in accordance with an embodiment of this disclosure.

FIG. 14 illustrates another example method 68 to improve the color-resolving ability of a user of a see-thru display device. Like method 52 of FIG. 5, this method may be enacted from within the see-thru display device, or in any other suitable manner.

At 58 an image of the real imagery sighted by the user is acquired. At 60 a locus of a color poorly distinguishable by the user is identified from the acquired image. At 62 first virtual imagery is constructed. Such imagery may be substantially the same as the virtual imagery referred to hereinabove—viz., virtual imagery to be superposed onto real imagery sighted by the user through the see-thru display device. As described hereinabove, this virtual imagery may be configured to accentuate a locus of the real imagery of a color poorly distinguishable by the user.

At 70 a request for second virtual imagery is received. The request may originate from an application or operating system running on the see-thru display device or elsewhere in the AR environment. The second virtual imagery may comprise virtually any desired image—text or graphics; it may or may not be related to the real imagery sighted by the user. At 72 the second virtual imagery is constructed.

In the embodiments contemplated herein, the second virtual imagery may be configured so that it is distinguishable by the user when superposed on the real imagery being sighted by the user. Suppose, for instance, that a deuteranomalous user is sighting real imagery of a predominately green color. This user may have difficulty resolving a red virtual image overlaid on such a background. In one embodiment, therefore, the see-thru display device may be configured to alter the display color of the requested second virtual imagery to make it more discernable to the color vision impaired user. Accordingly, red pixels of the requested second virtual imagery may be rendered violet, in one example. In a more particular embodiment, the second virtual imagery may be chosen to be distinguishable by the user when superposed on the real imagery together with the first virtual imagery.

At 66 the first and second virtual imagery constructed as described above are displayed. More particularly, the first and second virtual imagery are superposed onto the real imagery sighted by the user of the see-thru display device, in registry with the real imagery, in the user's field of view.

In some embodiments, the methods and processes described above may be tied to a computing system of one or more computing devices. In particular, such methods and processes may be implemented as a computer-application program or service, an application-programming interface (API), a library, and/or other computer-program product.

Figure 15:
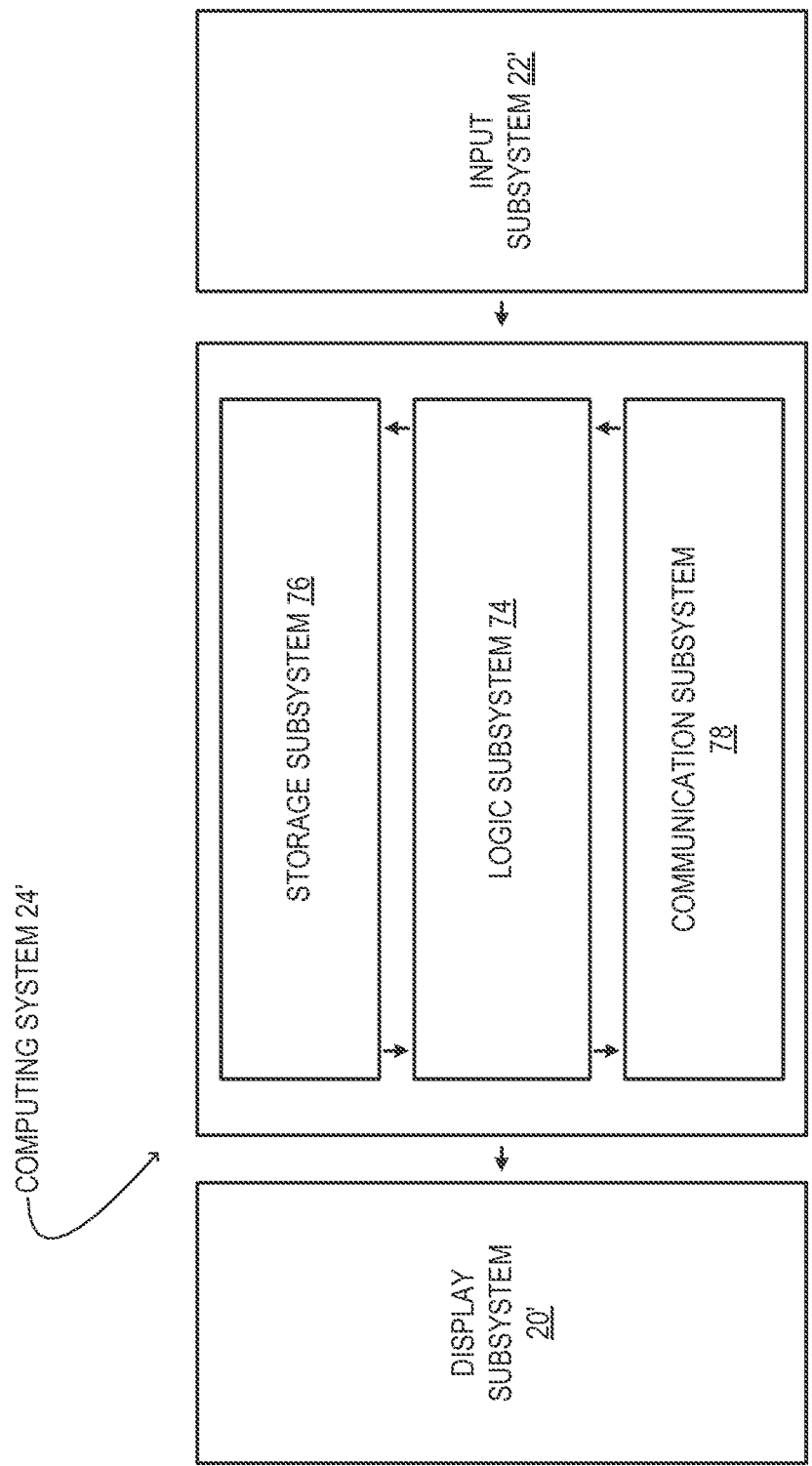
FIG. 15 schematically shows aspects of an example computing system in accordance with an embodiment of this disclosure.

FIG. 15 schematically shows a non-limiting embodiment of a computing system 24' that can enact one or more of the methods or processes described above. Computing system 24' is shown in simplified form. It will be understood that virtually any computer architecture may be used without departing from the scope of this disclosure. In different embodiments, computing system 24' may take the form of a mainframe computer, server computer, desktop computer, laptop computer, tablet computer, home-entertainment computer, network computing device, gaming device, mobile computing device, mobile communication device (e.g., smart phone), etc.

Computing system 24' includes a logic subsystem 74 and a storage subsystem 76. Computing system 24' may optionally include a display subsystem 20', input subsystem 22', communication subsystem 78, and/or other components not shown in FIG. 15.

Logic subsystem 74 includes one or more physical devices configured to execute instructions. For example, the logic subsystem may be configured to execute instructions that are part of one or more applications, services, programs, routines, libraries, objects, components, data structures, or other logical constructs. Such instructions may be implemented to perform a task, implement a data type, transform the state of one or more components, or otherwise arrive at a desired result.

The logic subsystem may include one or more processors configured to execute software instructions. Additionally or alternatively, the logic subsystem may include one or more hardware or firmware logic machines configured to execute hardware or firmware instructions. The processors of the logic subsystem may be single-core or multi-core, and the programs executed thereon may be configured for sequential, parallel or distributed processing. The logic subsystem may optionally include individual components that are distributed among two or more devices, which can be remotely located and/or configured for coordinated processing. Aspects of the logic subsystem may be virtualized and executed by remotely accessible networked computing devices configured in a cloud-computing configuration.

Storage subsystem 76 includes one or more physical, non-transitory, devices configured to hold data and/or instructions executable by the logic subsystem to implement the methods and processes described herein. When such methods and processes are implemented, the state of storage subsystem 76 may be transformed—e.g., to hold different data.

Storage subsystem 76 may include removable computer readable storage media and/or built-in devices. Storage subsystem 76 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard-disk drive, floppy-disk drive, tape drive, MRAM, etc.), among others. Storage subsystem 76 may include volatile, nonvolatile, dynamic, static, read/write, read-only, random-access, sequential-access, location-addressable, file-addressable, and/or content-addressable devices.

In some embodiments, aspects of logic subsystem 74 and of storage subsystem 76 may be integrated together into one or more hardware-logic components through which the functionally described herein may be enacted, at least in part. Such hardware-logic components may include field-programmable gate arrays (FPGAs), program- and application-specific integrated circuits (PASIC/ASICs), program- and application-specific standard products (PSSP/ASSPs), system-on-a-chip (SOC) systems, and complex programmable logic devices (CPLDs), for example.

It will be appreciated that storage subsystem 76 includes one or more physical, non-transitory devices. However, in some embodiments, aspects of the instructions described herein may be propagated in a transitory fashion by a pure signal—e.g., an electromagnetic or optical signal, etc.—that is not held by a physical device for a finite duration. Furthermore, data and/or other forms of information pertaining to the present disclosure may be propagated by a pure signal.

The term "program" may be used to describe an aspect of computing system 24' implemented to perform a particular function. In some cases, a program may be instantiated via logic subsystem 74 executing instructions held by storage subsystem 76. It will be understood that different programs may be instantiated from the same application, service, code block, object, library, routine, API, function, etc. Likewise, the same program may be instantiated by different applications, services, code blocks, objects, routines, APIs, functions, etc. The term "program" may encompass individual or groups of executable files, data files, libraries, drivers, scripts, database records, etc.

It will be appreciated that a "service", as used herein, is an application program executable across multiple user sessions. A service may be available to one or more system components, programs, and/or other services. In some implementations, a service may run on one or more server-computing devices.

When included, display subsystem 20' may be used to present a visual representation of data held by storage subsystem 76. This visual representation may take the form of a graphical user interface (GUI). As the herein described methods and processes change the data held by the storage subsystem, and thus transform the state of the storage subsystem, the state of display subsystem 20' may likewise be transformed to visually represent changes in the underlying data. Display subsystem 20' may include one or more display devices utilizing virtually any type of technology. Such display devices may be combined with logic subsystem 74 and/or storage subsystem 76 in a shared enclosure, or such display devices may be peripheral display devices.

When included, input subsystem 22' may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 78 may be configured to communicatively couple computing system 24' with one or more other computing devices. Communication subsystem 78 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 24' to send and/or receive messages to and/or from other devices via a network such as the Internet.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. In a see-thru display device, a method to address a color vision deficiency, the method comprising:
constructing virtual imagery to superpose onto a real world background viewable through the see-thru display device, where constructing the visual imagery includes identifying one or more loci of one or more real world objects of a color poorly distinguishable based upon the color deficiency and identifying a focal point of a user of the see-thru display device, the virtual imagery configured to accentuate the one or more loci such that loci nearer to the focal point are accentuated to a greater degree than loci farther from the focal point; and
displaying the virtual imagery such that the virtual imagery is superposed onto the one or more real world objects, in spatial registry with the one or more real world objects, in a field of view of the see-thru display device.

2. The method of claim 1 wherein the virtual imagery is configured to write one or more of text and a symbol adjacent the one or more loci.

3. The method of claim 1 further comprising acquiring an image of the real world background with a front-facing camera of the see-thru display device, wherein the virtual imagery is constructed based on the acquired image, and the one or more loci are identified from the acquired image.

4. The method of claim 1, further comprising presenting a visual color test, and receiving one or more user inputs in response to the visual color test.

5. The method of claim 1 further comprising receiving input that specifies the color poorly distinguishable, wherein constructing the virtual imagery includes accentuating one or more loci of the specified color of the one or more real world objects.

6. The method of claim 1 wherein constructing the virtual imagery includes identifying a plurality of loci of matching colors in the one or more real world objects and overwriting the loci with one or more of text, a symbol, and a segmentation pattern to indicate the matching colors.

7. The method of claim 1 wherein the virtual imagery includes first virtual imagery and second virtual imagery, the method further comprising:
identifying a first real world object and a second real world object in the real world background, where the first real world object is a recognized object and the second real world object is an unrecognized object; and
displaying the first virtual imagery such that the first virtual imagery is superposed onto the first real world object and displaying the second virtual imagery such that the second virtual imagery is superposed onto the second real world object, where the first real world object is accentuated differently than the second real world object.

8. The method of claim 7 wherein the second virtual imagery is chosen to be distinguishable when superposed on the first real world object together with the first virtual imagery.

9. The method of claim 1 wherein the first and second real world objects are recognized based on one or both of object color and object shape.

10. A see-thru display device configured to address a color-resolving ability of a user having a color vision deficiency, the see-thru display device comprising:
a front-facing camera configured to acquire an image of a real world background viewable through the see-thru display device;
a logic subsystem operatively coupled to a storage subsystem, the storage subsystem storing instructions that cause the logic subsystem to construct virtual imagery to superpose onto the real world background, the virtual imagery configured to accentuate one or more loci of one or more real world objects of a color poorly distinguishable based upon the color vision deficiency wherein constructing the virtual imagery includes identifying a plurality of loci of matching colors in the real world object and overwriting the loci with one or more of text, a symbol, and a segmentation pattern to indicate the matching colors;
an eye tracker configured to track a focal point of the user, wherein the virtual imagery is configured to accentuate a first locus nearer to the focal point to a greater degree, and accentuate a second locus farther from the focal point to a lesser degree; and
a microdisplay configured to display the virtual imagery such that the virtual imagery is superposed onto the one or more real world objects, in registry with the one or more real world objects, in a field of view of the see-thru display device.

11. The device of claim 10 further comprising a controllable dimming filter configured to controllably reduce a brightness of the real world background as sighted by the user.

12. The device of claim 10, where the instructions are executable to measure a length of time the user spends observing selected aspects of a scene in order to identify the color vision deficiency of the user.

13. The device of claim 10, where the instructions are executable to recognize one or more real world objects in the real world background, and where the virtual imagery is configured to accentuate loci of recognized real world objects differently from loci of unrecognized real world objects.

14. The device of claim 10, where the instructions are executable to recognize a first real world object and a second real world object in the real world background, and where the virtual imagery is configured to accentuate loci of the first real world object to a greater extent than loci of the second real world object based on a nature of the first real world object.

15. The device of claim 14, where the first real world object is a sign.

16. The device of claim 10, where the instructions are executable to receive an input from the user indicating a severity of the color vision deficiency.

17. The device of claim 10, where the instructions are executable to construct first virtual imagery for display to a first eye of the user and second virtual imagery for display to a second eye of the user, where the first virtual imagery accentuates loci of real world objects differently from the second virtual imagery.

18. In a see-thru display device, a method to improve a color-resolving ability of a user of the see-thru display device based upon a color vision deficiency of the user, the method comprising:

acquiring, with a front-facing camera of the see-thru display device, an image of a real world background viewable by the user through the see-thru display device;

recognizing a first real world object and a second real world object in the acquired image;

constructing virtual imagery to superpose onto the first and second real world objects, the virtual imagery configured to accentuate loci of the first and second real world objects having a color poorly distinguishable based upon the color vision deficiency, and constructed to accentuate loci of the first real world object to a greater extent than loci of the second real world object based on a nature of the first real world object; and displaying the virtual imagery such that the virtual imagery is superposed onto the first and second real world objects, in spatial registry with the first and second real world objects, in a field of view of the see-thru display device.

19. The method of claim 18 wherein the first real world object is a sign.

20. The method of claim 18 wherein the virtual imagery is configured to shift the color of the first and second real world objects.

* * * * *